(12) United States Patent
Coelingh Bennink et al.

(10) Patent No.: US 8,367,647 B2
(45) Date of Patent: Feb. 5, 2013

(54) TREATMENT OF MECONIUM ASPIRATION SYNDROME WITH ESTROGENS

(75) Inventors: Herman Jan Tijmen Coelingh Bennink, Werkhoven (NL); Monique Visser, Zeist (NL)

(73) Assignee: Pantarhei Bioscience B.V., Zeist (NL)

( * ) Notice: Subject to any disclaimer, the term of this patent is extended or adjusted under 35 U.S.C. 154(b) by 516 days.

(21) Appl. No.: 12/664,982

(22) PCT Filed: Jun. 20, 2008

(86) PCT No.: PCT/NL2008/050405
§ 371 (c)(1),
(2), (4) Date: Dec. 30, 2009

(87) PCT Pub. No.: WO2008/156365
PCT Pub. Date: Dec. 24, 2008

(65) Prior Publication Data
US 2010/0184736 A1   Jul. 22, 2010

(30) Foreign Application Priority Data
Jun. 21, 2007 (EP) .................................. 07110768

(51) Int. Cl.
*A61K 31/56* (2006.01)
(52) U.S. Cl. ........................................ 514/178; 514/182
(58) Field of Classification Search .................. None
See application file for complete search history.

(56) References Cited

U.S. PATENT DOCUMENTS

| 3,440,320 | A | 4/1969 | Sackler |
| 2003/0008012 | A1 | 1/2003 | Pena et al. |
| 2007/0071777 | A1 * | 3/2007 | Bromer et al. ............... 424/400 |

FOREIGN PATENT DOCUMENTS

| WO | 9849191 A1 | 11/1998 |
| WO | 0200330 A1 | 1/2002 |
| WO | 02094278 A | 11/2002 |
| WO | 2004037269 A | 5/2004 |
| WO | 2004110402 A | 12/2004 |

OTHER PUBLICATIONS

Trotter et al., "Effects of Postnatal Estradiol and Progesterone Replacement in Extremely Preterm Infants", Journal of Clinical Endocrinology and Metabolism, (Dec. 1999), vol. 84, No. 12, pp. 4531-4535.
Shanklin et al., "Aqueous Estrogens In The Management of Respiratory Distress Syndrome", Journal of Reproductive Medicine, (1970), vol. 5, No. 2, pp. 53-71.
Jakowicki, "Evaluation of Estriol Level In The Amniotic Fluid in Prolonged Pregnancy", DATABASE CA [Online], XP002458625, (1979).
Gorwill et al., "Unconjugated Serum Oestriol Levels in Mother and Baby With Meconium Staining of the Amniotic Fluid", British Journal of Obstetrics and Gynaecology, (Aug. 1978), vol. 85, No. 8, pp. 602-604.
Fogarty, "Postmaturity", Journal of the American Osteopathic Association, (1976), vol. 65, No. 5, pp. 512-517.
Jakowicki, "Evaluation of estriol level in the amniotic fluid in prolonged pregnancy", Ginekologia Polska (1979), pp. 167-168.

* cited by examiner

*Primary Examiner* — Bong-Sook Baek
(74) *Attorney, Agent, or Firm* — The Webb Law Firm

(57) ABSTRACT

One aspect of the present invention relates to the use of an estrogen in the treatment of Meconium Aspiration Syndrome (MAS) in a newborn infant, said treatment comprising administering an effective amount of estrogen to said newborn infant within 7 days after birth. The present treatment offers the advantage that estrogens can be administered using non-invasive modes of administration, e.g. oral or rectal administration. Other aspects of the present invention relate to a suppository for use in newborn infants comprising at least 1 μg of estrogen and to an oral applicator comprising a container holding an aqueous liquid containing micronised estetrol and a metering dispenser for metering the liquid into the oral cavity of a newborn infant.

14 Claims, No Drawings

TREATMENT OF MECONIUM ASPIRATION SYNDROME WITH ESTROGENS

TECHNICAL FIELD OF THE INVENTION

The present invention relates to a method of treating Meconium Aspiration Syndrome (MAS) in a newborn infant. Other aspects of the present invention relate to a suppository and an oral applicator for use in the aforementioned treatment of MAS in newborn infants.

BACKGROUND OF THE INVENTION

Meconium aspiration syndrome (MAS), also referred to as "Neonatal aspiration of meconium", occurs when infants inhale meconium into their lungs before or during delivery. Meconium is the first stool of an infant, composed of materials formed during the time the infant spends in the uterus: intestinal epithelial cells, lanugo, mucus, amniotic fluid, bile, and water. Meconium is sterile, unlike later faeces, and has no odour.

Meconium is normally stored in the infant's intestines until after birth, but sometimes (often in response to fetal distress) it is expelled into the amniotic fluid prior to birth during late stage pregnancy or during labour. If the baby then inhales the contaminated fluid, respiratory problems may occur.

Meconium passage into the amniotic fluid occurs in about five to twenty percent of all births. It is more common in postmature births. Meconium aspiration syndrome develops in 5-10 percent of these cases. About a third of those infants who experience MAS require breathing assistance. The mortality rate for MAS resulting from severe parenchymal pulmonary disease and pulmonary hypertension is as high as 20%. Other complications include air block syndromes (eg, pneumothorax, pneumomediastinum, pneumopericardium) and pulmonary interstitial emphysema.

Frequently, fetal distress during labour causes intestinal contractions, as well as a relaxation of the anal sphincter, which allows meconium to contaminate the amniotic fluid. Amniotic fluid is normally clear, but becomes greenish if it is tinted with meconium. If the infant inhales this mixture before, during, or after birth, it may be sucked deep into the lungs. Two main problems occur if this happens:

The material may block the airways. Complete obstruction of the airways by meconium results in atelectasis. Partial or intermittent obstruction causes air trapping and hyperdistention of the alveoli, commonly termed the ball-valve effect. Hyperdistention of the alveoli occurs from airway expansion during inhalation and airway collapse around inspissated meconium in the airway, causing increased resistance during exhalation. The gas that is trapped, hyperinflating the lung, may rupture into the pleura (pneumothorax), mediastinum (pneumomediastinum), or pericardium (pneumopericardium).

The meconium-tainted fluid is irritant, and results in inflammation of the airways which can lead to chemical pneumonia. Enzymes, bile salts, and fats in meconium irritate the airways and parenchyma, causing a release of cytokines and resulting in a diffuse pneumonia that may begin within a few hours of aspiration. All of these pulmonary effects can produce gross ventilation-perfusion (V-Q) mismatch. To complicate matters further, many infants with meconium aspiration syndrome (MAS) develop pulmonary hypertension of the newborn (PPHN) as a result of failure of the pulmonary vessels to dilate thereby lowering pulmonary vascular resistance and pulmonary artery pressures. Finally, though meconium is sterile, its presence in the air passages can predispose the infant to pulmonary infection.

The most obvious sign that meconium may have been aspirated is the greenish appearance of the amniotic fluid. The infant's skin may be stained green if the meconium was passed a considerable amount of time before birth. Rapid or laboured breathing, slow heartbeat, or low Apgar score are all signs of the syndrome. Inhalation can be confirmed by one or more tests such as using a stethoscope to listen for abnormal lung sounds, performing blood gas tests, and using chest X-rays to look for patchy or streaked areas on the lungs.

Although modern obstetric care has reduced the incidence of MAS, sudden unpredictable events occur during labour which stress the fetus to release meconium. Ensuring that the infant is born before 42 weeks of gestation may lessen the risk. Amnioinfusion is a method of thinning thick meconium that has passed into the amniotic fluid. In this procedure, a tube is inserted into the uterus through the vagina, and sterile fluid is pumped in to dilute thick meconium. Recent studies have not shown a benefit from amnioinfusion. Until recently it had been recommended that the throat and nose of the baby be suctioned by the obstetrician as soon as the head is delivered. However, new studies have shown that this is not useful and the revised Neonatal Resuscitation Guidelines published by the American Academy of Pediatrics no longer recommend it. When meconium staining of the amniotic fluid is present and the baby is born with depressed respiration, it is recommended that the pediatrician suction the mouth and nose and use a laryngoscope and suction catheter to suction meconium from below the vocal cords.

Other methods for treating MAS include surfactant instillation and surfactant lavage. WO 98/49191, for instance, describes a method for pulmonary lavage of a mammal suffering from MAS, said method comprising:

a) applying gas positive end-expiratory pressure (PEEP) with a ventilator into a lung section of said mammal at a pressure of from about 4 to 16 cm water;
b) instilling a lavage composition containing dilute surfactant in a pharmaceutically acceptable aqueous medium into said lung; and
c) removing pulmonary fluid from said lung using short intervals of tracheo-bronchial suction at a negative pressure of about 20 to 100 mm mercury.

Another method for treating MAS is described in WO 2004/075838 and comprises administering a complement inhibitor in the form of an antibody to a patient likely to develop or suffering from MAS. WO 2004/075858 teaches to administer the complement inhibitor to the lungs of the patient using inhalation or tracheal instillation.

The aforementioned methods suffer from the drawbacks that they are invasive and/or fail to effectively prevent or treat MAS.

SUMMARY OF THE INVENTION

The inventors have developed a method for the treatment of Meconium Aspiration Syndrome (MAS) that does not suffer from the drawbacks of the aforementioned prior art methods. The method according to the present invention comprises administering an effective amount of estrogen to a newborn infant within 7 days after birth.

Although the inventors do not wish to be bound by theory, it is believed that the beneficial effect of estrogen administration may be associated, amongst other things, with anti-inflammatory and vasodilative properties of estrogens.

An important advantage associated with the use of estrogens resides in the fact that estrogens can be administered using non-invasive modes of administration, e.g. oral or rectal administration. Furthermore, since up till the end of gestation newborns have been exposed to high levels of estrogens (notably estetrol, estriol and estradiol), adverse side-effects of estrogen administration are unlikely.

Administration of estrogens to premature infants has been suggested in the prior art. WO 2004/110402 describes intravenous administration of an oil-emulsion containing 17β-estradiol and progesterone to premature infants for postnatal hormone substitution. Trotter et al., J Clin Endocrinol Metab. 1999 December; 84(12): 4531-5 describe a study in which premature female infants received estradiol and progesterone replacement. The estradiol and progesterone replacement was started i.v. and was followed by transepidermal administration for a total duration of 6 weeks. The authors report that the incidence of chronic lung disease tended to be lower.

The present invention also provides a suppository for use in newborn infants comprising at least 1 μg of estrogen, said suppository further being characterized by a maximum diameter of less than 10 mm and a weight of less than 0.5 g. Suppositories containing a combination of estrogen and progestogen have been suggested in WO 02/00330, which is concerned with providing a method of contraception in mammalian females.

The invention further provides an oral applicator comprising a container holding a liquid and a metering dispenser for metering the liquid into the oral cavity of a newborn infant, wherein the liquid is an aqueous liquid containing at least 0.5 mg/ml of micronised estetrol.

DETAILED DESCRIPTION OF THE INVENTION

Accordingly, one aspect of the invention relates to the use of an estrogen in the treatment of Meconium Aspiration Syndrome (MAS) in a newborn infant, said treatment comprising administering an effective amount of estrogen to said newborn infant within 7 days after birth.

The present method is designed to treat newborn infants who are at risk of developing MAS, notably newborn infants whose amniotic fluid is stained with meconium. As explained herein before, amniotic fluid that is stained with meconium usually has a greenish colour.

As used herein the term "estrogen" refers to any pharmaceutically acceptable substance that is capable of triggering an estrogenic response by binding to an estrogen receptor. Examples of estrogens that may be employed in accordance with the present invention include estetrol, estriol, estradiol, estrone, ethinyl estradiol, mestranol, quinestranol, estran, conjugated equine estrogens, prodrugs of these compounds, and combinations of two or more of the aforementioned compounds.

According to a preferred embodiment, the present treatment employs a biogenic estrogen or a prodrug thereof. Particularly preferred biogenic estrogens include estetrol, estriol and estradiol. The aforementioned biogenic estrogens are usually prevalent in newborn infants in high concentrations. Shortly after delivery, however, plasma concentrations of these biogenic estrogens start to decrease rapidly. The present treatment effectively achieves that the high estrogen status found post partum in newborns is maintained for a period of time. Although the inventors do not wish to be bound by theory, it is believed that the high estrogen status of newborns somehow assists in protecting the infant against infections and hypoxia. By prolonging the high estrogen status, the present treatment is believed to protract the protective effect of said high estrogen status.

The inventors have found that the biogenic estrogen estetrol performs exceptionally well in the present treatment. This excellent performance of estetrol is believed to be associated with a surprisingly rapid onset of action of this estrogen. Furthermore, estetrol is believed to be a very potent vasodilator.

Best results are obtained with the present treatment if the estrogen is administered shortly after delivery. Accordingly, in a preferred embodiment, the estrogen is administered within 1 day after birth. Even more preferably, the estrogen is administered within 6 hours after birth. Most preferably the estrogen is administered within 1 hour after birth.

As explained, the benefits of estrogen administration in accordance with the present invention are highest when the estrogen is administered shortly after birth. Typically, the benefits of estrogen administration, irrespective of whether or not treatment was started shortly after delivery, become marginal after 90 days post partum. Accordingly, estrogen administration is preferably discontinued within 60 days after birth. Even more preferably, estrogen administration is discontinued within 30 days after birth.

The amount of estrogen to be administered depends, amongst other things, on the type of estrogen used as well as on the mode of administration. In case the present treatment employs synthetic estrogen, such as ethinyl estradiol, a dosage in the range of 1-50 μg will usually be adequate. In case of biogenic estogen or a prodrug thereof, the administered dosage preferably exceeds 0.1 mg. Even more preferably, biogenic estrogen or a prodrug thereof is administered in a dosage of 0.5-20 mg. According to another preferred embodiment the estrogen is administered in an amount equivalent to an oral dosage of at least 0.1 mg estetrol. Even more preferably, the estrogen is administered in an amount equivalent to an oral dosage of at least 0.5 mg estetrol.

In accordance with a preferred embodiment, the estrogen is administered at regular intervals, the duration of each interval being in the range of 6-24 hours. Most preferably, the estrogen is administered once daily for at least 3 days.

In order to achieve the medical benefits of the present treatment, the mode of administration is not critical. According to a preferred embodiment, however, the estrogen is administered orally, rectally or by injection, especially intravenous, subcutaneous, intramuscular or intratracheal injection. Most preferably, the estrogen is administered orally or rectally. The latter modes of administration offer the advantage that they are non-invasive and consequently less disturbing to the infant than, for instance, subcutaneous administration.

The treatment of MAS in accordance with the present invention is ideally suited for secondary prophylaxis, notably prophylaxis of severe complications of MAS, as it does not require invasive modes of administration and because the risk of undesired side effects is minimal. Hence, in accordance with a particularly advantageous embodiment, the present treatment is employed to prevent severe complications of MAS in a newborn infant suffering from MAS. Examples of severe complications of MAS include pneumothorax, pneumomediastinum, pneumopericardium, pulmonary interstitial emphysema, chemical pneumonia, gross ventilation-perfusion (V-Q) mismatch, pulmonary hypertension and pulmonary infection.

The present invention also encompasses therapeutic treatment of MAS in a newborn infant. Therapeutic treatment in accordance with the present invention may comprise administration of estrogen to a newborn infant exhibiting symptoms of chemical pneumonia or to a newborn infant suffering from hypoxia.

Another aspect of the present invention relates to a suppository for use in newborn infants comprising at least 1 μg of estrogen, said suppository further being characterized by a maximum diameter of less than 10 mm and a weight of less than 0.5 g. Typically, the suppository has a diameter in the range of 4-9 mm. The weight of the suppository is preferably in the range of 0.1-0.25 g. The excipient contained in the suppository may be based on lipid material that melts at body temperature or it may be based on a hydrophilic component that dissolves or disintegrates when it comes into contact with water. Most preferably, the excipient contained in the present suppository is based on a lipid material such as fat or glycerol. The suppository of the present invention is preferably bullet shaped.

According to a particularly preferred embodiment, the present suppository contains at least 0.1 mg, more preferably from 0.1-20 mg and most preferably from 0.5-5 mg of a biogenic estrogen or a prodrug thereof.

As explained herein before, the estrogen employed in the suppository is advantageously selected from the group consisting of estetrol, estriol, estradiol and combinations thereof. Most preferably, the estrogen is estetrol.

Yet another aspect of the invention relates to an oral applicator comprising a container holding a liquid and a metering dispenser for metering the liquid into the oral cavity of a newborn infant, wherein the liquid contains least 0.5 mg/ml, preferably 1-10 mg/ml and most preferably from 2 to 5 mg/ml estetrol.

According to a particularly preferred embodiment, the liquid containing the estetrol is an aqueous liquid. In case an aqueous liquid is employed in the present applicator, it is preferred to use estetrol in micronised form.

The metering dispenser of the present oral applicator preferably is a pipette designed for metering out drops of 0.02-0.08 ml.

The invention is further illustrated by means of the following non-limiting examples.

EXAMPLES

Example 1

Immediately after birth, twelve newborn piglets are given 3 ml/kg of a 20% solution of human meconium by deep intratracheal instillation. Next, the piglets are randomly assigned to two groups of each six animals. Within one hour after birth, one group is treated with a daily oral dosage of 0.7 mg/kg estetrol whilst the control group is treated with placebo. During the next 7 days the condition of the piglets belonging to both groups are monitored. It is found that the incidence of severe complications of MAS is substantially lower in the group of animals that was treated with estetrol than in the control group.

Example 2

Example 1 was repeated, except that this time one group was treated with a daily oral dosage of 30 μg/kg estradiol instead of estetrol. Again, a lower incidence of severe complications of MAS is found in the group of animals treated with the estrogen than in the control group.

The invention claimed is:

1. A method of treating Meconium Aspiration Syndrome (MAS) in a newborn infant, said method comprising administering an effective amount of estrogen to said newborn infant within 7 days after birth, wherein the estrogen is selected from the group consisting of estetrol, estriol, estradiol and combination thereof.

2. The method according to claim 1, wherein the estrogen is administered within 1 day after birth.

3. The method according to claim 1, wherein the estrogen is administered within 6 hours after birth.

4. The method according to claim 1, wherein the estrogen is administered within 1 hour after birth.

5. The method according to claim 1, wherein the estrogen administration is discontinued within 90 days after birth.

6. The method according to claim 1, wherein the estrogen administration is discontinued within 30 days after birth.

7. The method according to claim 1, wherein the estrogen is administered orally, rectally or by injection.

8. The method according to claim 7, wherein the estrogen is administered orally or rectally.

9. The method according to claim 8, wherein the estrogen is administered rectally.

10. The method according to claim 1, wherein the estrogen is administered to prophylactically treat severe complications of MAS.

11. The method according to claim 1, wherein the newborn infant exhibits symptoms of chemical pneumonia.

12. The method according to claim 1, wherein the newborn infant is suffering from hypoxia.

13. The method according to claim 1, wherein the estrogen is administered in an amount equivalent to an oral dosage of at least 0.1 mg estetrol.

14. The method according to claim 13, wherein the estrogen comprises at least estetrol.

\* \* \* \* \*

UNITED STATES PATENT AND TRADEMARK OFFICE
CERTIFICATE OF CORRECTION

PATENT NO.      : 8,367,647 B2
APPLICATION NO. : 12/664982
DATED           : February 5, 2013
INVENTOR(S)     : Coelingh Bennink et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 523 days.

Signed and Sealed this
First Day of September, 2015

Michelle K. Lee
*Director of the United States Patent and Trademark Office*